(12) United States Patent
Vernon (10) Patent No.: US 7,852,052 B2
(45) Date of Patent: Dec. 14, 2010

(54) SUPPLY CIRCUIT FOR IMPLANTABLE MEDICAL DEVICES

(75) Inventor: Scott D. Vernon, Chandler, AZ (US)

(73) Assignee: Medtronic, Inc., Minneapolis, MN (US)

( * ) Notice: Subject to any disclaimer, the term of this patent is extended or adjusted under 35 U.S.C. 154(b) by 1108 days.

(21) Appl. No.: 11/363,770

(22) Filed: Feb. 28, 2006

(65) Prior Publication Data

US 2007/0203528 A1 Aug. 30, 2007

(51) Int. Cl.
*G05F 1/00* (2006.01)
*H02J 3/46* (2006.01)
*A61N 1/00* (2006.01)

(52) U.S. Cl. ............................. 323/269; 307/24; 607/4

(58) Field of Classification Search .................. 323/269, 323/270, 272; 307/24; 607/4, 9, 12
See application file for complete search history.

(56) References Cited

U.S. PATENT DOCUMENTS

| | | | |
|---|---|---|---|
| 3,924,641 A | 12/1975 | Weiss | |
| 4,343,312 A | 8/1982 | Cals et al. | |
| 4,345,604 A * | 8/1982 | Renirie | 607/34 |
| 4,402,322 A | 9/1983 | Duggan | |
| 4,406,286 A | 9/1983 | Stein | |
| 4,416,282 A | 11/1983 | Saulson | |
| 4,476,868 A | 10/1984 | Thompson | |
| 5,233,985 A | 8/1993 | Hudrlik | |
| 5,782,880 A | 7/1998 | Lahtinen et al. | |
| 6,044,296 A | 3/2000 | Zhu et al. | |
| 6,968,231 B1 | 11/2005 | Silivian et al. | |

FOREIGN PATENT DOCUMENTS

WO WO/03039648 A 5/2003

OTHER PUBLICATIONS

International Search Report, PCT/US/2007/062374, Jul. 31, 2007, 6 Pages.

* cited by examiner

*Primary Examiner*—Bao Q Vu
*Assistant Examiner*—Jue Zhang
(74) *Attorney, Agent, or Firm*—Carol F. Barry (57) ABSTRACT

A supply circuit for an implantable medical device (IMD) is presented. The supply circuit includes a battery, a high current circuit, a current-modifying component, a low current circuit, and a capacitor. The low current circuit is connected to a first terminal of the battery. A current-modifying component is connected to the battery, a capacitor, and to a high current circuit.

4 Claims, 13 Drawing Sheets

SUPPLY CIRCUIT FOR IMPLANTABLE MEDICAL DEVICES

FIELD OF THE INVENTION

The present invention generally relates to an implantable medical device (IMD), and more particularly, to a supply circuit in an IMD.

BACKGROUND OF THE INVENTION

Implantable medical devices (IMDs) detect, diagnose, and deliver therapy for a variety of medical conditions in patients. IMDs include implantable pulse generators (IPGs) or implantable cardioverter-defibrillators (ICDs) that deliver electrical stimuli to tissue of a patient. ICDs typically comprise, inter alia, a control module, a capacitor, and a battery that are housed in a hermetically sealed container. When therapy is required by a patient, the control module, which includes a supply circuit, signals the battery to charge the capacitor. The capacitor then discharges electrical stimuli to tissue of a patient.

During discharge of the battery to the capacitor, battery droop may occur. Battery droop involves the battery output voltage quickly dropping to a sub-nominal voltage (e.g. 1.8 volts). Thereafter, the output voltage slowly increases or recovers to near no-load voltage potential as the capacitor becomes fully charged. It is desirable to eliminate excessive battery droop since it can disturb the operation of other circuits in the IMD.

DETAILED DESCRIPTION

The following description of embodiments is merely exemplary in nature and is in no way intended to limit the invention, its application, or uses. For purposes of clarity, the same reference numbers are used in the drawings to identify similar elements.

The present invention is directed to a supply circuit for an implantable medical device (IMD). The supply circuit includes a battery, a current-modifying component, at least one high current circuit, at least one low current circuit, and a capacitor. A terminal (e.g. positive (+) terminal) of a battery is connected to the low current circuit, a current-modifying component, a high current circuit, and a capacitor. The capacitor is connected between the high current circuit and a fixed voltage. When the high current circuit draws current, the capacitor is discharged, while the current-modifying component prevents excessive battery droop so that operation of the low current circuit is not significantly affected. After a high current event the capacitor is charged in preparation for the next high current event.

In addition to preventing excessive battery droop, supply circuits of the present invention assist in eliminating at least four large capacitors from three-chamber (i.e. atrial, right ventricle, and left ventricle) cardiac-related IMDs. Elimination of these capacitors reduces the cost and the complexity of the supply circuits.

Figure 1:
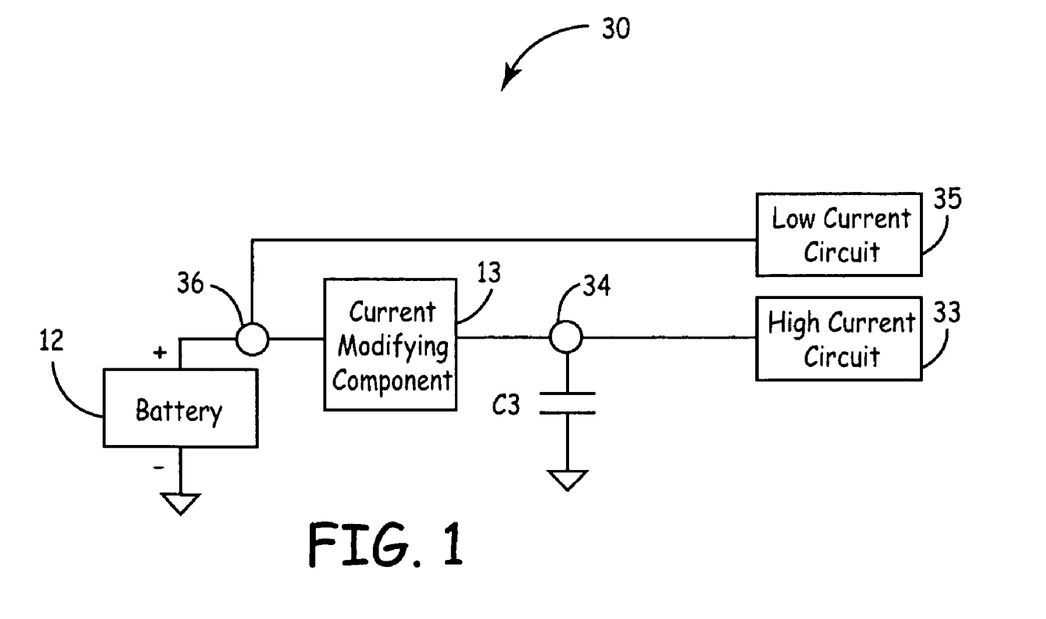
FIG. 1 is a schematic diagram of one embodiment of a supply circuit for an IMD.

FIG. 1 depicts a schematic diagram of one embodiment of a supply circuit 30. Supply circuit 30 includes battery 12 (e.g. low or medium rate batteries), a current-modifying component 13, a capacitor C3, at least one high current circuit 33 (also referred to as a first circuit), and at least one low current circuit 35 (also referred to as a second circuit). At node 36, low current circuit 35, configured to receive less than or equal to 100 microamperes, is connected to the output terminal or positive (+) terminal of battery 12.

Current-modifying component 13 affects the flow of current to high current circuit 33. Current-modifying component 13, at node 36, is connected to the output terminal of battery 12. At node 34, current-modifying component 13 is also connected to capacitor C3, and a high current circuit 33. High current circuit 33 is configured to receive greater than or equal to 1 miliamperes of current. Capacitor C3 and the negative (−) terminal of battery 12 are connected to a fixed voltage (e.g. ground).

In operation, before high current (e.g. several milliamps etc.) is drawn by high current circuit 33, capacitor C3 is charged to the voltage of battery 12. When the high current circuit 33 draws current, the voltage across capacitor C3 is depleted, but current-modifying component 13 provides sufficient resistance to prevent a significant change in the voltage across battery 12.

Figure 2:
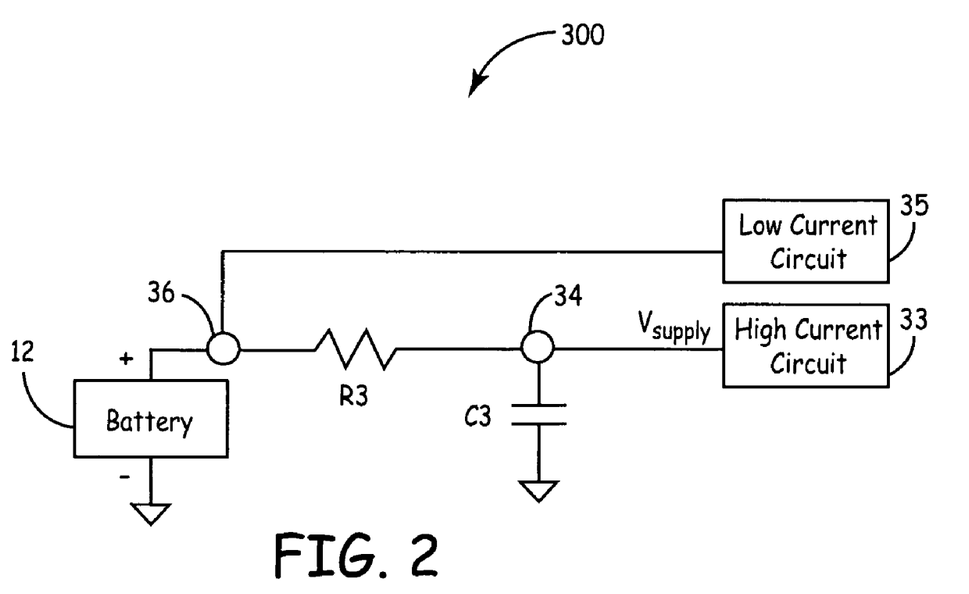
FIG. 2 is a schematic diagram of another embodiment of a supply circuit for an IMD.

FIGS. 2 through 11 depict a variety of electronic components that are considered current-modifying components 13. For example, resistor R3, depicted in supply circuit 300 of FIG. 2, is considered a current-modifying component 13. R3 includes a resistance value (e.g. 10 Kilo (K) ohms) that is sufficiently high that the voltage across battery 12 is substantially stable when current is drawn at node 34, but the resistance value is also sufficiently low to allow capacitor C3 to be charged relatively quickly between high current events.

Capacitor C3 can be drained by a relatively high current and/or long duration of current without significantly affecting the voltage supplied to low current circuit 35. At node 34, the voltage can fall below the battery output voltage. Therefore, supply circuit 300 is suitable for configurations in which the high current circuit 33 is able to at least temporarily tolerate a supply voltage (Vsupply) lower than the battery output voltage. Skilled artisans appreciate that the amount of voltage by which high current circuit 33 is exposed to a Vsupply lower than the battery output voltage depends upon the capacitance value of capacitor C3.

Figure 3:
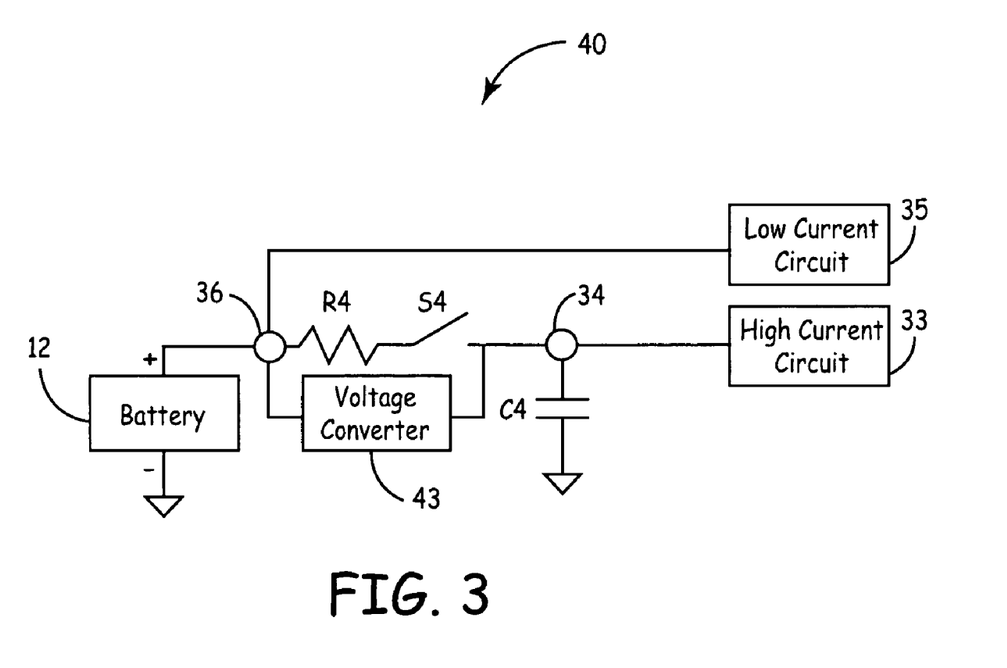
FIG. 3 is a schematic diagram of yet another embodiment of a supply circuit for an IMD.

FIG. 3 is a schematic diagram of another embodiment of supply circuit 40. Supply circuit 40 includes battery 12, resistor R4, switch S4 (e.g. a PMOS transistor), capacitor C4, voltage converter 43, high current circuit 33, and a low current circuit 35. Essentially, current-modifying-component 13 of FIG. 1 is replaced by voltage converter 43, resistor R4 and switch S4. Skilled artisans understand that many electronic components may serve as voltage converter 43. Voltage converter 43 may be, for example, a capacitor-based charge pump. Alternatively, voltage converter 43 may be a switching regulator utilizing magnetic components such as inductors and transformers.

Voltage converter 43 includes an input terminal connected to battery 12 and an output terminal connected at node 34 to capacitor C4 and to high current circuit 33. Capacitor C4 is also connected a fixed voltage (such as ground). Resistor R4 and switch S4 are connected in series between nodes 34 and 36. Resistor R4 and switch S4 are connected in parallel to voltage converter 43.

In operation, before a high current is drawn by high current circuit 33, switch S4 is opened and capacitor C4 is charged to a voltage that is higher than the voltage supplied by battery 12. During this pre-charging operation, the current from battery 12 is sufficiently low (e.g. 100 microamperes (uA)) that low current circuit 35 is not disturbed by the voltage drop across the internal source impedance of battery 12. The voltage drop across the internal source impedance is equal to the pre-supply current multiplied by battery source resistance. In some embodiments, an additional capacitor is connected, at node 36, between the output terminal of battery 12 and the fixed voltage (i.e., ground). Typically, the additional capacitor is selected to have a much smaller capacitance value than that of capacitor C4. For example, the additional capacitor can be 1 microfarad (uF) and C4 can be 22 uF.

When high current circuit 33 draws current, capacitor C4 is depleted to a voltage which may be above, below, or equal to the voltage supplied by battery 12 (depending on the amount and duration of current drawn). If capacitor C4 is depleted to a voltage that is less than or equal to the battery voltage, switch S4 is closed to recharge capacitor C4 to voltage of battery 12. Resistor R4 (e.g. 10K ohms) prevents excessive battery droop during this recharge operation. If capacitor C4 remains at a voltage higher than the battery voltage, there are a couple of options. First, switch S4 can be closed, if battery 12 is able to tolerate current flow into its positive terminal. Second, the voltage can be left in capacitor C4 in preparation for the next high current event. The voltage in capacitor C4 eventually decreases, due to internal capacitor leakage and/or due to a small current drawn from high current circuit 33. Once the voltage in capacitor C4 falls to the battery voltage, switch S4 can be closed.

Supply circuit 40 allows the voltage provided to the high current circuit 33 to be sustained above or equal to the battery voltage. This configuration provides the ability to draw a greater amount and/or duration of current from capacitor C4, due to the higher voltage stored in capacitor C4 prior to the high current event.

Both supply circuit 30 (FIG. 1) and supply circuit 40 (FIG. 3) draw current at a relatively low level from battery 12 while the capacitor (i.e. C3 or C4), provides the high current to high current circuit 33. Once the capacitor is charged, high current can be drawn quickly from the capacitor (i.e. C3 or C4), leaving the battery voltage relatively unaffected. Supply circuits 30 and 40 are particularly effective in applications where high current circuit 33 operates at a relatively low duty cycle, as is the case in many IMDs (e.g. implantable cardioverter-defibrillators (ICDs)). This allows the capacitor to be fully replenished by a long duration, low amplitude current (e.g. 100 uA) from battery 12 between high current events, with the small amplitude of the current ensuring that battery 12 output voltage is maintained sufficiently stable so as not to disturb the operation of low current circuit 35. Supply circuits 30 and 40 produce large short-duration current to some circuits in the IMD, while preventing excessive battery droop in the voltage supplied to low current circuit 35. Supply circuits 30 and 40 also isolate the drooping effect to the capacitor that supplies current to high current circuit 33 only, leaving the voltage supplied to the low current circuit 35 relatively intact and stable.

Figure 4:
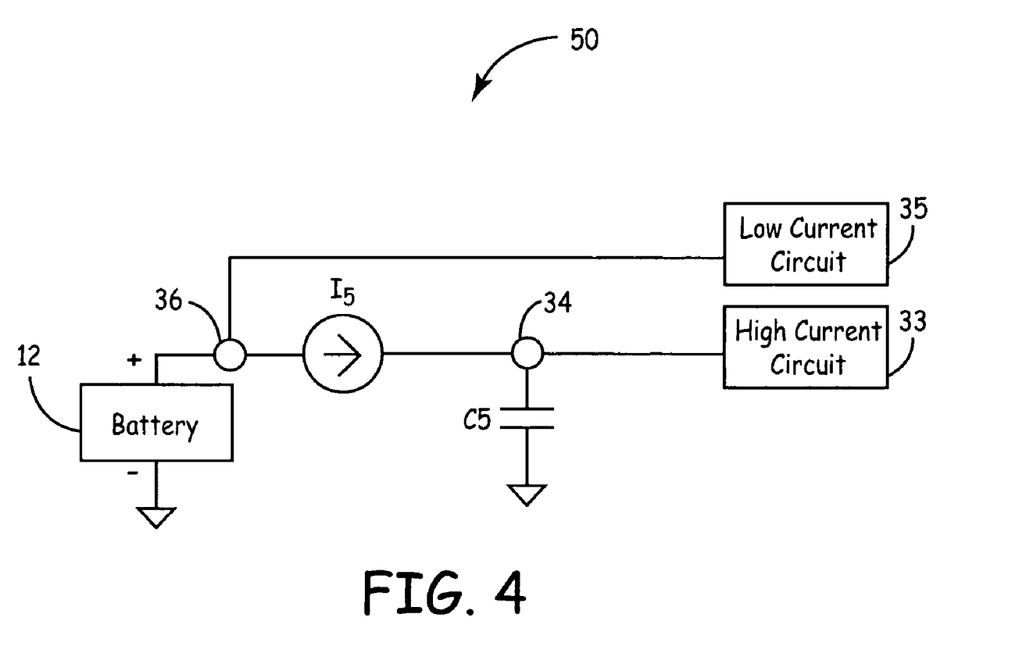
FIG. 4 is a schematic diagram of still yet another embodiment of a supply circuit for an IMD.

FIG. 4 is a schematic diagram of another embodiment of a supply circuit 50. Supply circuit 50 includes battery 12, a current source $I_5$, a capacitor C5, high current circuit 33, and low current circuit 35. Current source $I_5$ is connected between battery 12 and capacitor C5 at nodes 36 and 34 respectively. Capacitor C5 is also connected to a fixed voltage (such as ground).

Supply circuit 50 operates in a similar manner as supply circuit 300, except that current source $I_5$ replaces resistor R3. Current source $I_5$ behaves in a manner similar to a resistor or a voltage source when the voltage drop across current source $I_5$ is relatively small such as on the order of several hundreds of millivolts (mV), which is the typical operating condition of supply circuit 50. In a typical embodiment, current source $I_5$ maximizes the speed of recharging capacitor C5 following a high current event while maintaining the battery droop below a given threshold (e.g. 100 millivolt (mV)).

Figure 5:
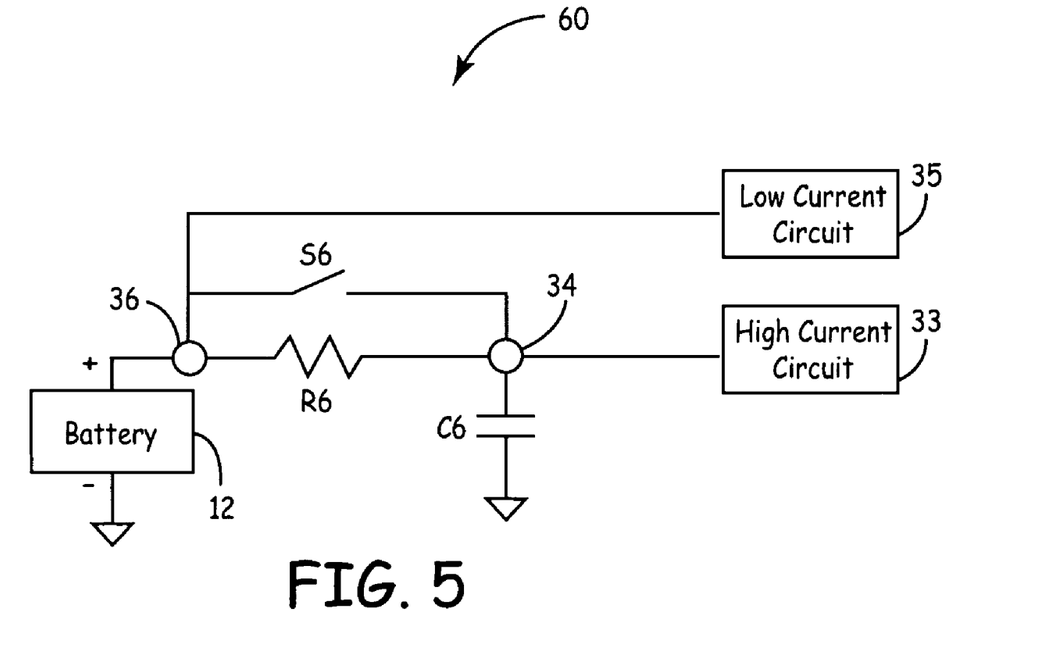
FIG. 5 is a schematic diagram of another embodiment of a supply circuit for an IMD.

FIG. 5 is a schematic diagram of a yet another supply circuit 60. Supply circuit 60 includes battery 12, resistor R6, switch S6, capacitor C6, high current circuit 33, and second circuit 35. Resistor R6 and switch S6 are connected in parallel between battery 12 and capacitor C6. Capacitor C6 is also connected to a fixed voltage (such as ground).

Supply circuit 60 operates in a similar manner as circuit 300, except that switch S6 is in parallel with resistor R6 and is closed after capacitor C6 is recharged back to the level of the battery voltage. Supply circuit 60 increases the decoupling capacitance when switch S6 is closed for the low current circuit 35. Supply circuit 60 also provides a lower direct current (DC) source resistance (i.e., battery 12) when the high current circuit 33 is not drawing high current but instead requires some low level operating current (e.g. 100 uA).

Figure 6:
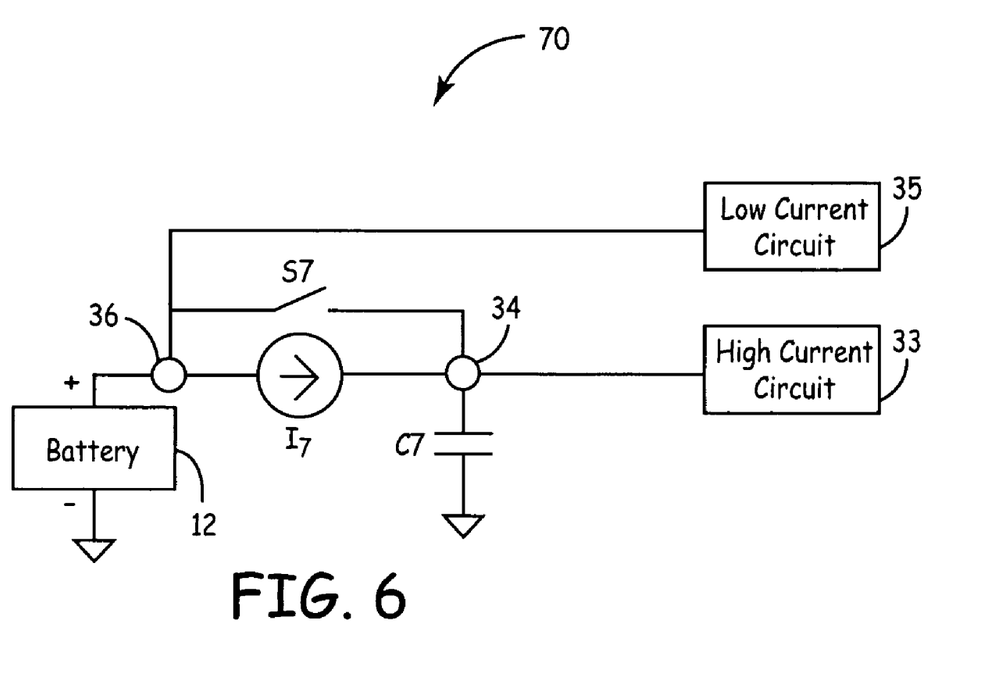
FIG. 6 is a schematic diagram of another embodiment of a supply circuit for an IMD.

FIG. 6 is a schematic diagram of another supply circuit 70. Supply circuit 70 includes battery 12, current source $I_7$, switch S7, capacitor C7, high current circuit 33, and low current circuit 35. Current source $I_7$ and switch S7 are connected in parallel between nodes 34, and 36. Capacitor C7 is connected between node 34 and a fixed voltage (such as ground). Circuit 70 operates in a similar manner as circuit 60 shown, except that resistor R7 in circuit 60 is replaced with current source $I_7$.

Figure 7:
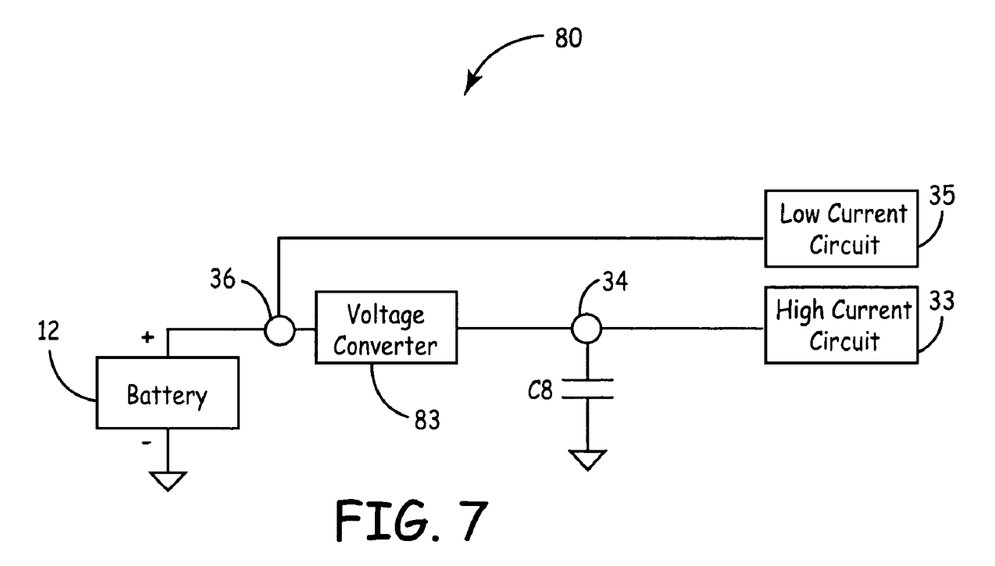
FIG. 7 is a schematic diagram of yet another embodiment of a supply circuit for an IMD.

FIG. 7 is a schematic diagram of still yet another embodiment of supply circuit 80. Supply circuit 80 includes battery 12, voltage converter 83, capacitor C8, high current circuit 33, and low current circuit 35. Voltage converter 83 has an input terminal connected to node 36 and an output terminal connected to node 34. Capacitor C8 is connected between node 34 and a fixed voltage (such as ground).

Supply circuit 80 operates in a similar manner as supply circuit 40 except that voltage converter 83 of circuit 80 is the only mechanism that provides current to high current circuit 33. Supply circuit 80 is simplified in architecture and has a low number of components, but is less power efficient because voltage converter 83 is the only way that current is provided to the high current circuit 33.

Figure 8:
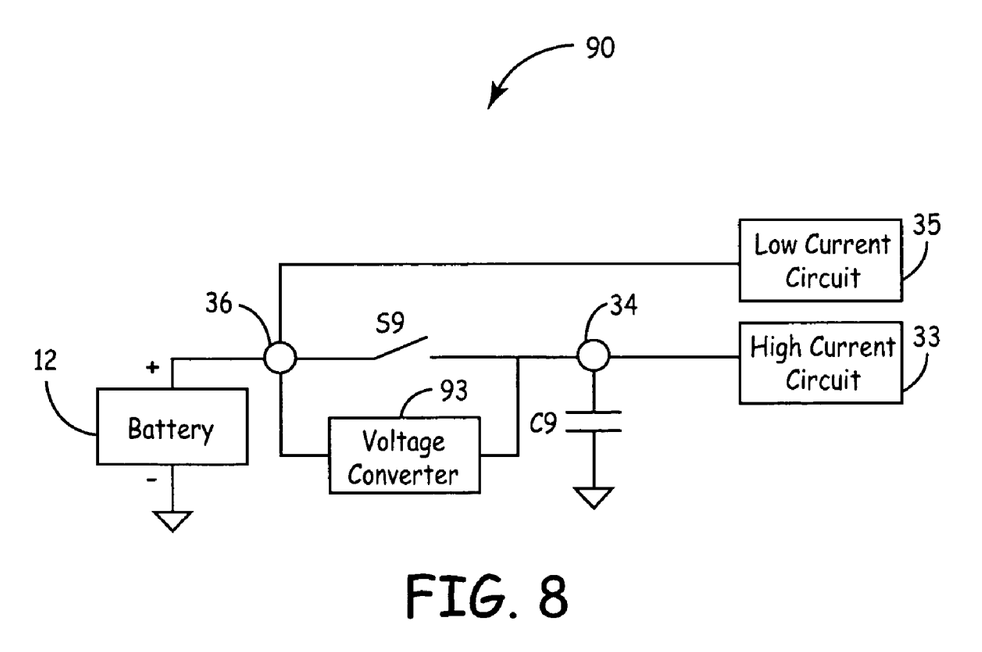
FIG. 8 is a schematic diagram of still yet another embodiment of a supply circuit for an IMD.

FIG. 8 is a schematic diagram of another embodiment of supply circuit 90. Supply circuit 90 includes battery 12, switch S9, voltage converter 93, capacitor C9, high current circuit 33, and low current circuit 35. Switch S9 is connected in parallel to voltage converter 93. Voltage converter 93 includes an input terminal connected to battery 12 at node 36 and an output terminal connected to capacitor C9 and high current circuit 33 at node 34. Capacitor C9 is also connected to a fixed voltage (such as ground).

Supply circuit 90 shown in FIG. 8 operates in a similar manner as supply circuit 40 except that no resistor is connected in series with switch S9. In order to effectively implement supply circuit 90, switch S9 is carefully controlled based on the relative voltages between nodes 34 and 36 to ensure that switch S9 is only closed when the voltage at the output and input to voltage converter 93 are nearly equal. This prevents spikes in the voltage at node 36 and prevents current from flowing back into battery 12.

Figure 9:
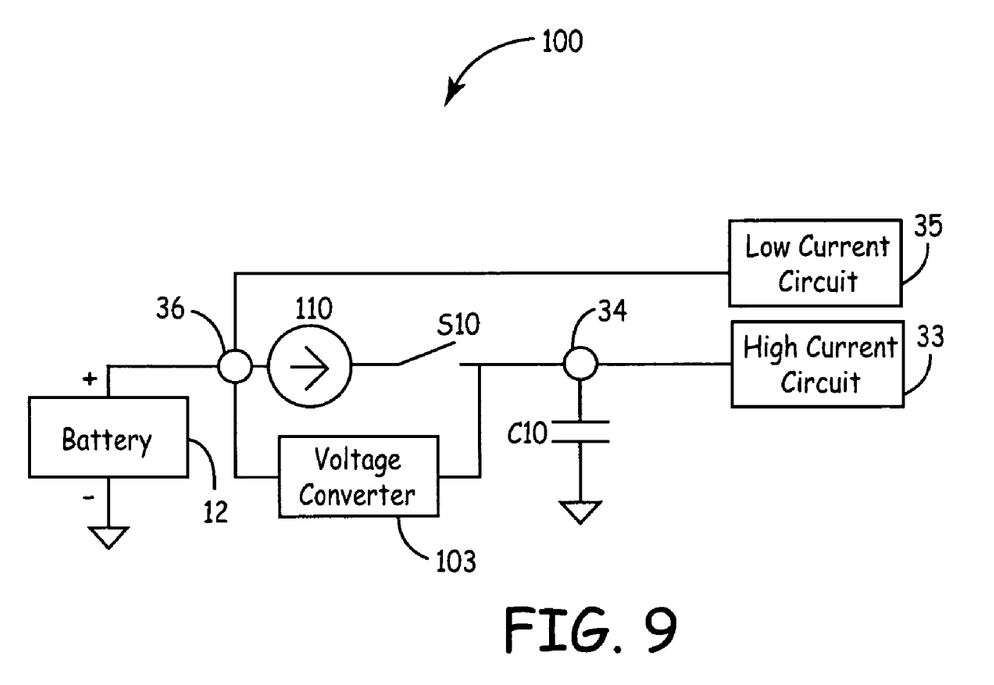
FIG. 9 is a schematic diagram of another embodiment of a supply circuit for an IMD.

FIG. 9 is a schematic diagram of another embodiment of a supply circuit 100. Supply circuit 100 includes battery 12, current source 110, switch S10, voltage converter 103, capacitor C10, high current circuit 33, and low current circuit 35. Current source 110 and switch S10 are connected in series between nodes 34, 36. Current source 110 and switch S10 are connected in parallel to voltage converter 103. Voltage converter 103 has an input terminal connected battery 12 at node 36 and an output terminal connected to capacitor C10 and high current circuit 33 at node 34. Capacitor C10 is also connected to a fixed voltage (such as ground).

Supply circuit 100 operates in a similar manner as circuit 40, except that current source 110 replaces resistor R4. As previously discussed, utilizing a current source in place of a resistor maximizes the speed of recharging a capacitor while ensuring excessive battery droop does not occur.

Figure 10:
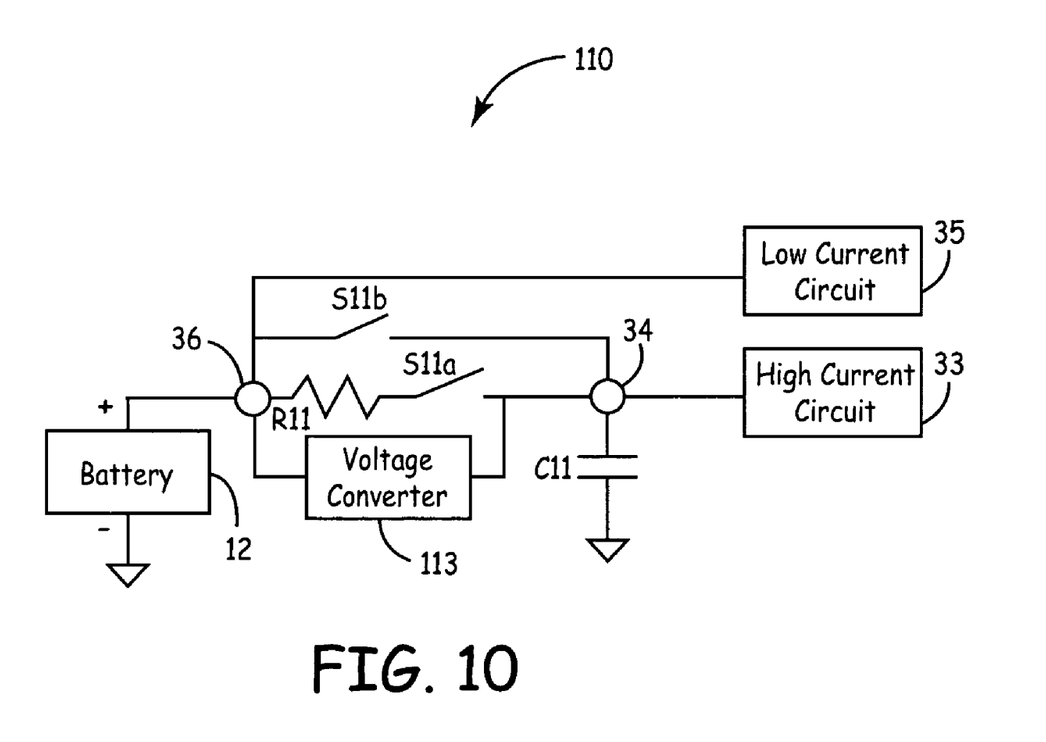
FIG. 10 is a schematic diagram of still yet another embodiment of a supply circuit for an IMD.

FIG. 10 is a schematic diagram of yet another embodiment of supply circuit 110. Supply circuit 110 includes battery 12, resistor R11, switches S11a and S11b, voltage converter 113, capacitor C11, high current circuit 33, and low current circuit 35. Resistor R11 and switch S11a are connected in series between nodes 34 and 36. Switch S11b is also connected between nodes 34 and 36. Voltage converter 113 has an input terminal connected at node 36 and an output terminal connected at node 34. Capacitor C11 is connected at node 34 and a fixed voltage (such as ground).

Supply circuit 110 operates in a similar manner as supply circuit 40 except switch S11b is connected in parallel between nodes 34 and 36. Switch 11b allows high current circuit 33 to be supplied directly via battery 12 when current demand is sufficiently low (e.g. 100 uA), which is more power efficient than providing current through voltage converter 113.

Figure 11:
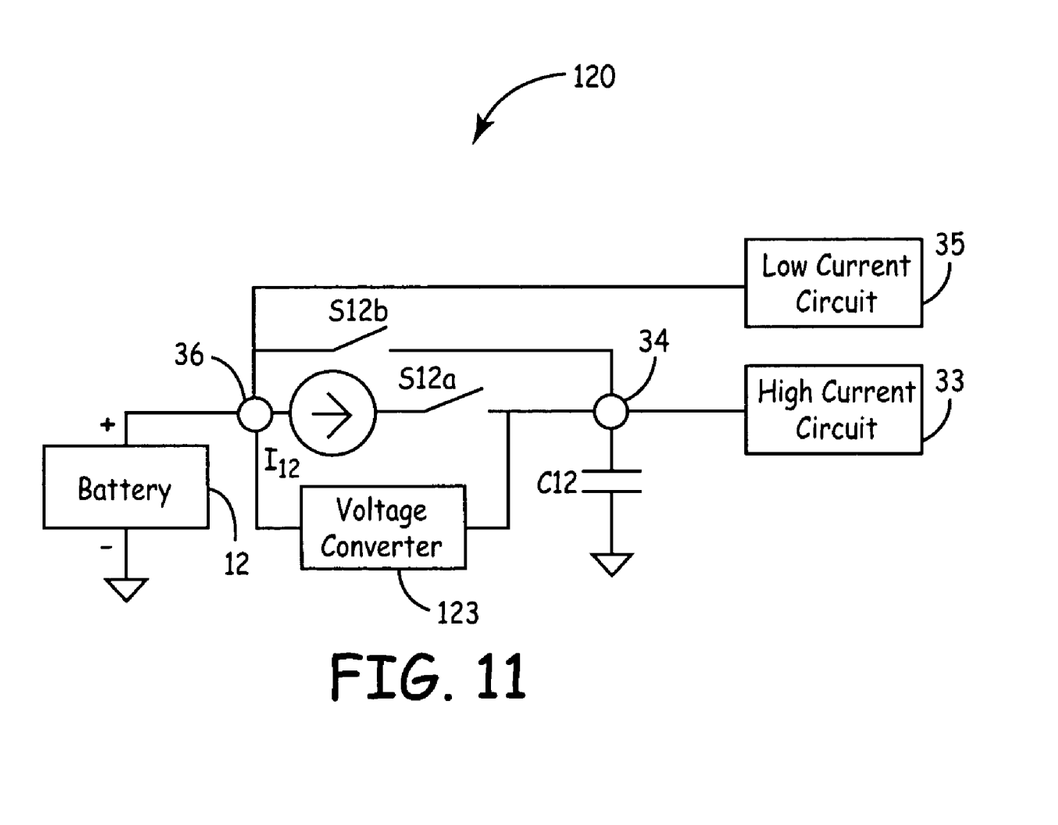
FIG. 11 is a schematic diagram of a yet another embodiment of a supply circuit for an IMD.

FIG. 11 is a schematic diagram of another embodiment of supply circuit 120. Supply circuit 120 includes battery 12, current source $I_{12}$, switches S12a and S12b, voltage converter 123, capacitor C12, high current circuit 33, and low current circuit 35. Current source $I_{12}$ and switch S12a are connected in series between nodes 34 and 36. Switch S12b is connected in parallel to $I_{12}$ and switch S12a. Voltage converter 123 has an input terminal connected to node 36 and an output terminal connected to node 34. Capacitor C12 is connected between node 34 and a fixed voltage (such as ground).

Supply circuit 120 operates in a similar manner as supply circuit 110 except that current source $I_{12}$ replaces resistor R11. Current source $I_{12}$ maximizes the speed of recharging capacitor C5 following a high current event while maintaining the battery droop below a given threshold (e.g. 100 mV).

Figure 12:
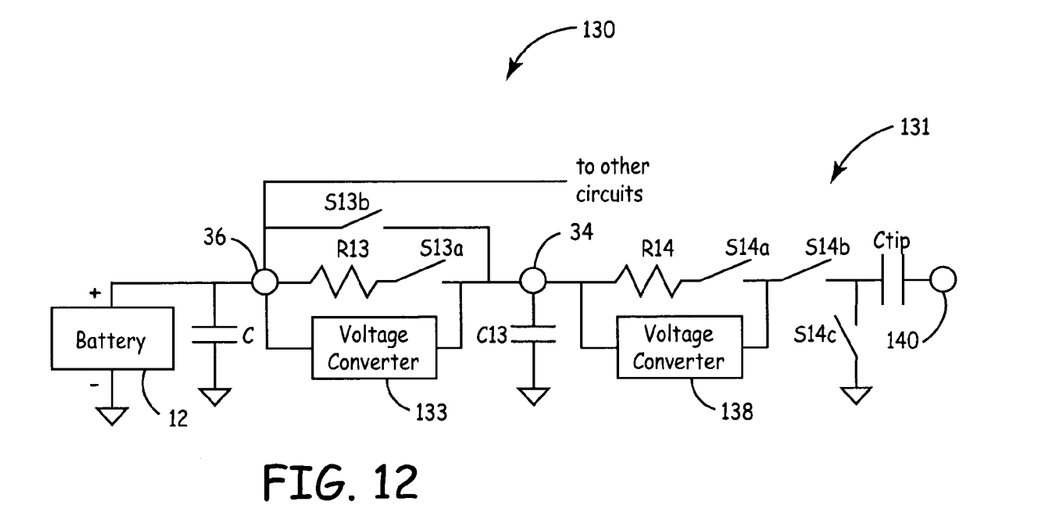
FIG. 12 is a schematic diagram that depicts an exemplary application of a control module for an IMD.

FIG. 12 is a schematic diagram that exemplifies an application of control module 130. Control module 130 includes battery 12, resistor R13, switches S13a and S13b, voltage converter 133, capacitors C and C13 (with capacitor C connected between the positive terminal (+) of battery 12 and a fixed voltage such a ground), node 34 connected to high current circuit 131, and node 36 connected to other low current circuit 35. High current circuit 131 is a shown as a pace delivery circuit, although it should be understood that other high current circuits (such as microprocessors, telemetry circuits, or others) could also be included in circuit 131. Circuit 131 includes resistor R14, switches S14a, S14b and S14c, voltage converter 138, and tip capacitor Ctip connected to heart load node 140.

In operation, switches S14a, S14b and S14c of circuit 131 are selectively activated to provide pacing signals to the heart. An example of the operation of a pace delivery circuit such as circuit 131 is disclosed in U.S. application Ser. No. 11/141, 975 filed May 31, 2005 for "Apparatus for Tissue Stimulation" by S. Vernon and L. Tyler, which is incorporated by reference in relevant parts. Circuit 130 is operated as described above, with a high current drawn from capacitor C13 when pace delivery circuit 131 is activated, and with a relatively low current being provided by battery 12 to charge capacitor C13 between high current events. As described above, this configuration provides the necessary current while preventing excessive battery droop. Circuit 130 is configured to meet the high current demands of pace delivery circuit 131 while also reliably supplying power to low current circuit 35 so that their operation is not compromised.

Figure 13:
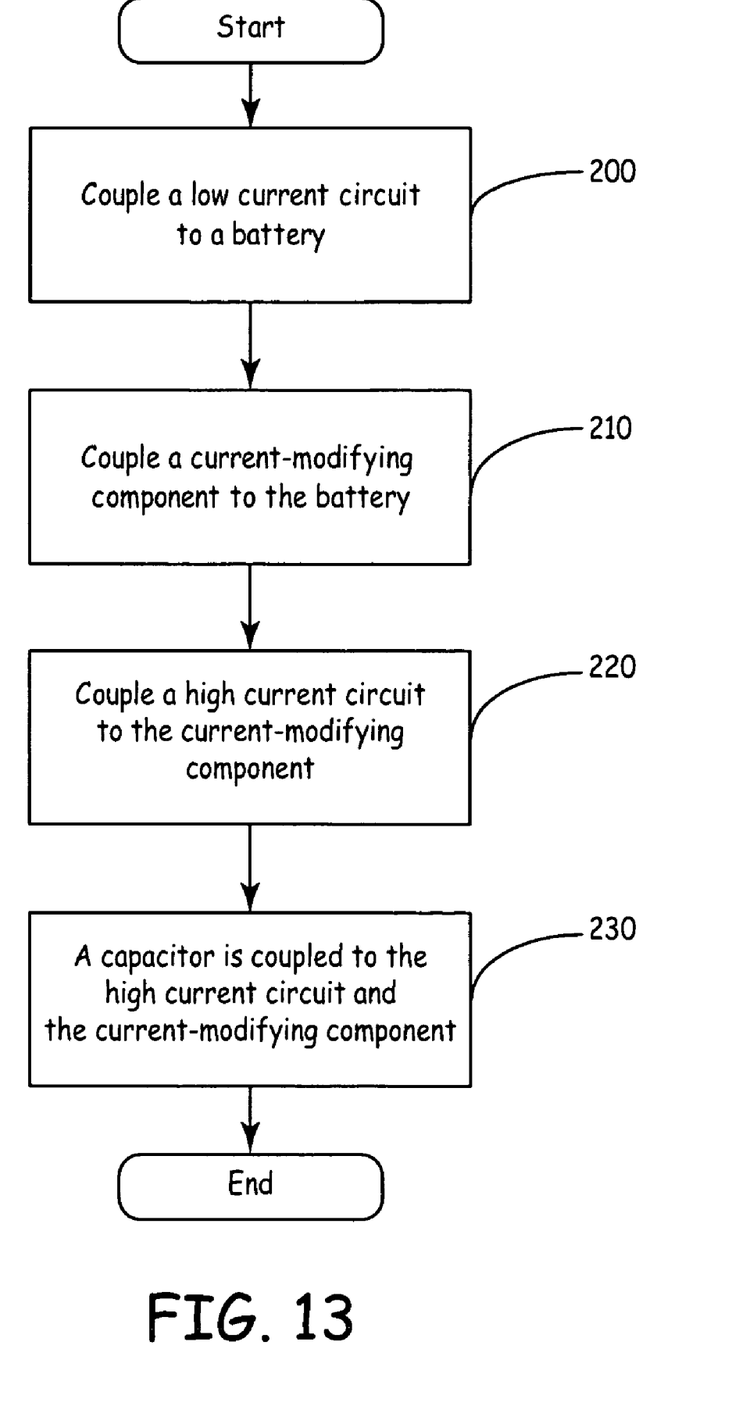
FIG. 13 is a flow diagram that depicts controlling current through a supply circuit.

FIG. 13 is a flow diagram for controlling current in a supply circuit for an IMD. At block 200, a low current circuit is coupled to a battery. At block 210, a current-modifying component is coupled to the battery. At block 220, a high current circuit is coupled to the current-modifying component. At block 230, a capacitor is coupled to the current-modifying component, the high current circuit, and a fixed voltage.

The above-described embodiments of a supply circuit have been configured with a battery connected to provide high current to high current circuits and to provide lower current to other circuits. In alternative embodiments, power may be supplied to the lower current circuits via another mechanism, such as by a voltage regulator connected between the high current circuit node and the low current circuit node.

Although the present invention has been described with reference to various embodiments, workers skilled in the art will recognize that changes may be made in form and detail without departing from the spirit and scope of the invention. For example, one skilled in the art will recognize that other types of medical devices, in addition to the examples described herein, can be employed in various embodiments while practicing the principles of the invention.

The invention claimed is:

1. A supply circuit for an implantable medical device (IMD) comprising:
   a battery;
   a low current circuit coupled to the battery;
   a current-modifying component coupled to the battery;
   a high current circuit coupled to the current-modifying component; and
   a capacitor coupled to the current-modifying component and to the high current circuit
   wherein the current-modifying component comprises:
   a resistor and a switch connected in series between the battery and the capacitor; and
   a voltage converter which includes an input terminal and an output terminal, the input terminal connected to the battery and the output terminal connected to the capacitor, wherein the resistor and the switch are in parallel with the voltage converter.

2. A supply circuit for an implantable medical device (IMD) comprising:
- a battery;
- a low current circuit coupled to the battery;
- a current-modifying component coupled to the battery;
- a high current circuit coupled to the current-modifying component; and
- a capacitor coupled to the current-modifying component and to the high current circuit wherein the current-modifying component comprises:
- a resistor and a first switch connected in series between the battery and the capacitor;
- a second switch connected in parallel with the resistor and the first switch between the battery and the capacitor; and
- a voltage converter having an input terminal connected to the battery and an output terminal connected to the capacitor.

3. A method of controlling current in a supply circuit for an implantable medical device (IMD) comprising:
- providing a battery;
- coupling a low current circuit to the battery;
- coupling a current-modifying component to the battery;
- coupling a capacitor to the current-modifying component and a fixed voltage; and
- coupling a high current circuit to the current-modifying component and to the capacitor, wherein the current modifying component being:
- a resistor and a first switch connected in series between the battery and the capacitor;
- a second switch connected in parallel with the resistor and the first switch between the battery and the capacitor; and
- a voltage converter having an input terminal connected to the battery and an output terminal connected to the capacitor.

4. A method of controlling current in a supply circuit for an implantable medical device (IMD) comprising:
- providing a battery;
- coupling a low current circuit to the battery;
- coupling a current-modifying component to the battery;
- coupling a capacitor to the current-modifying component and a fixed voltage; and
- coupling a high current circuit to the current-modifying component and to the capacitor, wherein the current path from the battery to the first node being established by:
- a current source and a first switch connected in series between the battery and the capacitor;
- a second switch connected in parallel with the current source and the first switch between the battery and the capacitor; and
- a voltage converter having an input terminal connected to the battery and an output terminal connected to the capacitor.

* * * * *